United States Patent [19]

Schleppnik

[11] 3,984,354

[45] Oct. 5, 1976

[54] 1-(3'-HEXENYL)-1-CYCLOALKANOLS AND THEIR ESTERS

[75] Inventor: Alfred A. Schleppnik, St. Louis, Mo.

[73] Assignee: Monsanto Company, St. Louis, Mo.

[22] Filed: Dec. 30, 1974

[21] Appl. No.: 537,504

Related U.S. Application Data

[62] Division of Ser. No. 212,780, Dec. 27, 1971, Pat. No. 3,857,898.

[52] U.S. Cl. ................................ 252/522; 260/410; 260/469; 260/476 R; 260/488 R

[51] Int. Cl.² ........................ A61K 7/46; C11B 9/00

[58] Field of Search ............ 260/488 R, 476 R, 469, 260/410; 252/522

[56] References Cited

UNITED STATES PATENTS

| | | | |
|---|---|---|---|
| 3,743,671 | 7/1973 | Teisseire et al. | 252/522 |
| 3,769,330 | 10/1973 | Nikawitz et al. | 260/488 R |
| 3,890,370 | 6/1975 | Buchi et al. | 252/522 |

*Primary Examiner*—C. Davis

*Attorney, Agent, or Firm*—Howard C. Stanley; Neal E. Willis; J. E. Maurer

[57] ABSTRACT

1-(3'-Hexenyl)-1-cycloalkanols and their esters characterized by the structural formula

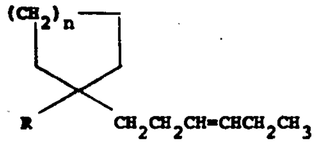

wherein R represents hydroxyl or $R^1COO$—, wherein $R^1$ represents alkyl having from 1 to 8 carbon atoms, aryl or aralkyl and n is an integer from 1 to 3. These compounds can be in the cis or trans forms or mixtures thereof. The compounds have very pleasant, strong and long lasting green, floral, rosy aromas and are useful as fragrances or as components in fragrance compositions.

15 Claims, No Drawings

1-(3'-HEXENYL)-1-CYCLOALKANOLS AND THEIR ESTERS

This is a division of application Ser. No. 212,780 filed Dec. 27, 1971, now U.S. Pat. No. 3,857,898.

This invention relates to the art of fragrance compositions and, more particularly, to a novel class of compounds possessing a characteristic aroma. More specifically, this invention is directed to a novel class of useful compounds, (their preparation and the utility of these compounds as fragrances or as components in fragrance compositions.

The art of perfumery began, perhaps, in the ancient cave dwellings of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed a large number of synthetic odoriferous chemicals possessing aroma characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Accordingly, there is a great need in the art of fragrance compositions for new compounds possessing specific characteristic aromas.

The principle object of the present invention is to provide a new class of aroma chemicals consisting of 1-(3'-hexenyl)-1-cycloalkanols and their esters.

Another object of the present invention is to provide a specific class of compounds having a characteristic aroma which is utilized in the preparation of fragrances and fragrance compositions.

These and other objects, aspects and advantages of this invention will become apparent from a consideration of the accompanying specification and claims.

In accordance with the above objects, there is provided by the present invention a novel class of compounds characterized by the structural formula

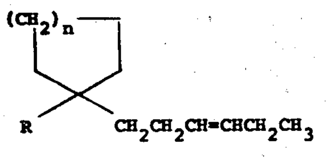

wherein R represents hydroxyl or $R^1COO-$, wherein $R^1$ represents alkyl having from 1 to 8 carbon atoms, aryl and aralkyl and *n* is an integer from 1 to 3.

These compounds have very pleasant, strong and long lasting green, floral, rosy aromas and are useful as fragrances or as components in fragrance compositions.

Representative alkyl groups characterized by $R^1$ in the above formula include methyl, ethyl, n-propyl, i-propyl, n-butyl, i-butyl, tert-butyl, n-amyl, i-amyl, tert-amyl, n-octyl.

Groups other than alkyl characterized by $R^1$ in the above formula include phenyl, naphthyl and phenylalkyl and the like.

It should be understood that the scope of the present invention encompasses both the cis and trans forms, as well as mixtures thereof, of the novel compounds of this invention. The precursor compounds can be the cis, trans or mixtures of both as desired to provide the compounds of this invention.

The novel cycloalkanols of this invention are prepared by reacting a cycloalkanone characterized by the structural formula

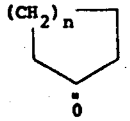

wherein *n* has the same meaning as defined hereinbefore, with 3-hexenyl magnesium halides as illustrated in the following equation (wherein X represents a halogen, chlorine, bromine or iodine):

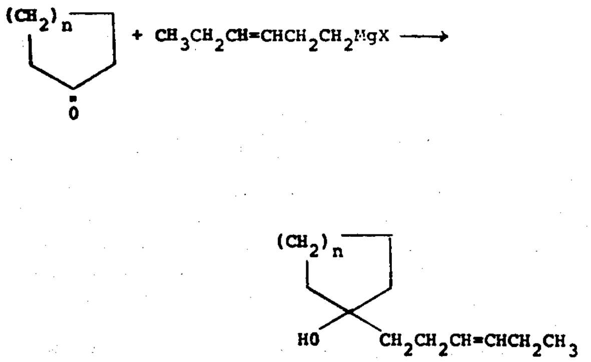

The novel esters of this invention can be prepared by reacting the 1-(3'-hexenyl)-1-cycloalkanols with an appropriate organic acid as illustrated in the following equation:

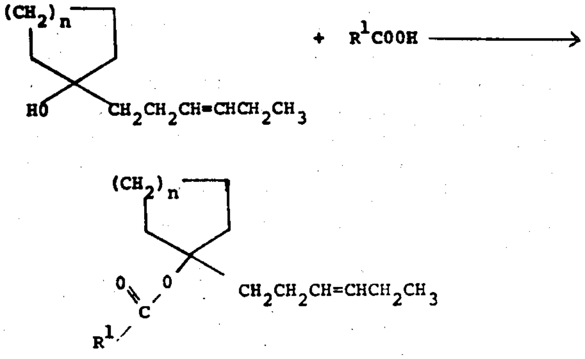

wherein $R^1$ and $n$ have the same meaning as defined hereinabove.

The reaction conditions are not critical but should be such as to facilitate the preparation of the products. Thus, the Grignard reaction is normally conducted at a temperature of from ambient temperatures up to about 150°C. and the esterification reaction is normally conducted within this same range.

The novel compounds of this invention are useful as fragrances in the preparation and formulation of fragrance compositions such as perfumes and perfumed products due to their pleasing, strong and long lasting aroma. Perfume compositions and the use thereof in cosmetic, detergent and bar soap formulations and the like are exemplary of the utility thereof. Likewise, these novel compounds can be utilized as the primary fragrance in many such compositions.

The compounds of this invention are used in concentrations of from trace amounts up to about 50 percent of the fragrance composition into which they are incorporated. As will be expected, the concentration of the compound will vary depending on the particular fragrance desired in the composition and even within the same composition when compounded by different perfumers.

The following examples will serve to illustrate certain specific embodiments within the scope of this invention and are not to be construed as limiting the scope thereof.

EXAMPLE 1

1-(3′-hexenyl)-1-cyclopentanol 12.2 Grams of magnesium were mixed with 50 ml. of anhydrous tetrahydrofuran and activated with 0.5 ml. of methyl iodide. To this mixture was added a solution of 59.3 grams (0.5 moles) of cis-1-chloro-3-hexene in 150 ml. of tetrahydrofuran. The hexene solution was added drop-wise with stirring. A greenish turbid solution formed but no exothermic reaction took place. The reaction was initiated by warming the mixture containing about one-third of the halide solution to 55°C. and adding a few drops of methyl iodide. A fast exothermic reaction started which was controlled with a cold water bath to keep the temperature at about 50°C. A clear brown solution formed.

To this solution a solution of 42.1 grams (0.5 moles) of cyclopentanone in 70 ml. ether can be added at such a rate that the mixture will reflux gently. After the addition is completed the product obtained, after fractional distillation, will be 1-(3′-hexenyl)-1-cyclopentanol.

EXAMPLE 2

1-(3′-hexenyl)-1-cyclohexanol

Following a procedure similar to the procedure described in Example 1 but substituting cyclohexanone for cyclopentanone results in the formation of the title compound.

EXAMPLE 3

1-(3′-hexenyl)-1-cycloheptanol

Following a procedure similar to Example 1 but substituting cycloheptanone for cyclopentanone results in the formation of the title compound.

EXAMPLE 4

The compounds of Examples 1, 2 and 3 can be reacted with equimolar amounts of acetic anhydride in pyridine to form the acetate ester of the cycloalkanols.

While the invention has been described herein with regard to certain specific embodiments, it is not so limited. It is to be understood that variations and modifications thereof may be made by those skilled in the art without departing from the spirit and scope of the invention.

The embodiments of this invention in which an exclusive property or privilege is claimed are defined as follows:

1. A compound characterized by the structural formula

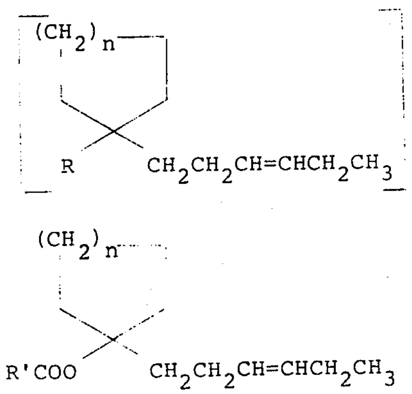

wherein R′ is alkyl with from 1 to 8 carbon atoms, aryl or aralkyl and $n$ is an integer of from 1 to 3.

2. A compound as defined in claim 1 wherein $n$ is 1.

3. A compound as defined in claim 1 wherein $n$ is 2.

4. A compound as defined in claim 1 wherein $n$ is 3.

5. A compound as defined in claim 1 which is 1-(3′-hexenyl)-1-cyclopentyl acetate.

6. A compound as defined in claim 1 which is 1-(3′-hexenyl)-1-cyclohexyl acetate.

7. In the method of preparing a fragrance composition, the step comprising incorporating therein an odoriferous amount of a compound as defined in claim 1.

8. The method of claim 7 wherein the compound incorporated is 1-(3′-hexenyl)-1-cyclopentanol.

9. The method of claim 7 wherein the compound incorporated is 1-(3′-hexenyl)-1-cyclohexanol.

10. A fragrance composition having incorporated therein an odoriferous amount of a compound as defined in claim 1.

11. A fragrance composition as defined in claim 10 wherein the compound incorporated is 1-(3′-hexenyl)-1-cyclopentanol.

12. A fragrance composition as defined in claim 10 wherein the compound incorporated is 1-(3′-hexenyl)-1-cyclohexanol.

13. In a method of providing a composition with a fragrance, the step comprising incorporating therein an odoriferous amount of a compound as defined in claim 1.

14. The method is defined in claim 13 wherein the compound incorporated is 1-(3′-hexenyl)-1-cyclopentanol.

15. The method as defined in claim 13 wherein the compound incorporated is 1-(3′-hexenyl)-1-cyclohexanol.

* * * * *

UNITED STATES PATENT OFFICE

CERTIFICATE OF CORRECTION

PATENT NO. : 3,984,354

DATED : October 5, 1976

INVENTOR(S) : Alfred A. Schleppnik

It is certified that error appears in the above-identified patent and that said Letters Patent are hereby corrected as shown below:

Claim 1, formula in brackets ([ ]), should have been deleted.

Signed and Sealed this

Third Day of May 1977

[SEAL]

*Attest:*

RUTH C. MASON
*Attesting Officer*

C. MARSHALL DANN
*Commissioner of Patents and Trademarks*